US012810977B2

(12) United States Patent
Ramanathan et al.

(10) Patent No.: US 12,810,977 B2
(45) Date of Patent: Nov. 24, 2026

(54) METHOD AND SYSTEM FOR DISTRIBUTING AND ACCESSING DIAGNOSTIC IMAGES ASSOCIATED WITH DIAGNOSTIC IMAGING REPORT

(71) Applicant: RAMSOFT INC., Toronto (CA)

(72) Inventors: Vijay Ramanathan, Toronto (CA); Selvin Jebaraj Selvapandian, Toronto (CA)

(73) Assignee: Ramsoft Inc., Toronto (CA)

( * ) Notice: Subject to any disclaimer, the term of this patent is extended or adjusted under 35 U.S.C. 154(b) by 0 days.

(21) Appl. No.: 18/801,050

(22) Filed: Aug. 12, 2024

(65) Prior Publication Data

US 2024/0404663 A1 Dec. 5, 2024

Related U.S. Application Data

(62) Division of application No. 14/529,119, filed on Oct. 30, 2014, now abandoned.

(51) Int. Cl.
*G16H 10/60* (2018.01)
*G06F 16/13* (2019.01)
(Continued)

(52) U.S. Cl.
CPC ............. *G16H 10/60* (2018.01); *G06F 16/13* (2019.01); *G06F 16/58* (2019.01); *G06F 16/5838* (2019.01); *G06F 16/5846* (2019.01); *G06F 16/587* (2019.01); *G06F 16/9554* (2019.01); *G06F 16/9566* (2019.01);
(Continued)

(58) Field of Classification Search
CPC ...... G06F 19/321; G06F 19/322; G06F 16/13; G06F 16/58; G06F 16/5838; G06F 16/5846; G06F 16/587; G06F 16/9554; G06F 16/9566; H04N 1/00334; H04N 23/00; G16H 30/40; G16H 10/60; G16H 30/20
See application file for complete search history.

(56) References Cited

U.S. PATENT DOCUMENTS

| | | | |
|---|---|---|---|
| 2009/0084713 A1 | 4/2009 | Miller et al. | |
| 2012/0035963 A1* | 2/2012 | Qian | G16H 30/20 705/3 |

(Continued)

OTHER PUBLICATIONS

Non-Final Office Action dated May 4, 2017, issued in related U.S. Appl. No. 14/529,119 (24 pages).

(Continued)

*Primary Examiner* — Chad A Newton
(74) *Attorney, Agent, or Firm* — Sheppard Mullin Richter & Hampton LLP

(57) ABSTRACT

Methods and systems for distributing and accessing diagnostic images associated with a diagnostic imaging report are disclosed. A DICOM server is configured to receive diagnostic images and diagnostic information from an imaging facility based on a diagnostic imaging study. The received diagnostic images and diagnostic information are stored at a DICOM storage of the server. A diagnostic imaging report is generated based on diagnostic report input parameters related to the received diagnostic images and the diagnostic information. The generated diagnostic imaging report includes a barcode containing an embedded file path to one or more of the received diagnostic images.

5 Claims, 5 Drawing Sheets

(51) Int. Cl.

| | |
|---|---|
| ***G06F 16/58*** | (2019.01) |
| ***G06F 16/583*** | (2019.01) |
| ***G06F 16/587*** | (2019.01) |
| ***G06F 16/955*** | (2019.01) |
| ***G16H 30/20*** | (2018.01) |
| ***H04N 1/00*** | (2006.01) |
| *H04N 23/00* | (2023.01) |

(52) U.S. Cl.

CPC ......... *G16H 30/20* (2018.01); *H04N 1/00334* (2013.01); *H04N 23/00* (2023.01)

(56) References Cited

U.S. PATENT DOCUMENTS

| | | | | | |
|---|---|---|---|---|---|
| 2012/0179908 | A1* | 7/2012 | Duma | G16H 10/65 | 713/165 |
| 2012/0316948 | A1* | 12/2012 | Shipley | G06Q 30/02 | 705/14.1 |
| 2013/0173915 | A1* | 7/2013 | Haulund | H04L 63/18 | 713/155 |
| 2014/0143337 | A1* | 5/2014 | McIntosh | H04L 61/50 | 709/204 |
| 2015/0205919 | A1* | 7/2015 | Robertson | G16H 10/60 | 705/3 |

OTHER PUBLICATIONS

Final Office Action dated Sep. 7, 2018, issued in related U.S. Appl. No. 14/529,119 (21 pages).

Non-Final Office Action dated Mar. 30, 2021, issued in related U.S. Appl. No. 14/529,119 (26 pages).

* cited by examiner

METHOD AND SYSTEM FOR DISTRIBUTING AND ACCESSING DIAGNOSTIC IMAGES ASSOCIATED WITH DIAGNOSTIC IMAGING REPORT

CROSS REFERENCE TO RELATED APPLICATION

The present application is a divisional application of U.S. patent application Ser. No. 14/529,119, filed on Oct. 30, 2014, entitled "Method and System for Distributing and Accessing Diagnostic Images Associated with Diagnostic Imaging Report," the content of which is hereby incorporated by reference in its entirety.

TECHNICAL FIELD

The present disclosure relates generally to diagnostic imaging. More particularly, some embodiments relate to systems and methods for distributing and accessing digital diagnostic images associated with a hardcopy diagnostic imaging report.

DESCRIPTION OF THE RELATED ART

Diagnostic imaging is a process used to create visual representations of the interior of a patient's body for clinical analysis and medical intervention. After acquiring medical images associated with an ordered diagnostic imaging procedure, an interpreting physician creates a diagnostic report. These diagnostic reports are provided to the patient and/or physicians in hard copy format. In conventional systems for distributing diagnostic reports, the diagnostic images associated with the report are provided to the patient and physicians on a portable digital recording medium such as CD or DVD or in hardcopy format such as film or paper. More recently, conventional systems also make the diagnostic images available via a secure online portal that requires a secured login of an authorized viewer of the report.

Security and convenience are desired attributes in a diagnostic report distribution system. However, conventional systems suffer from problems, particularly with respect to the distribution of diagnostic images associated with the report. For example, in systems where diagnostic images are only available as film prints or on portable digital recording mediums, access to the images is only available through the parties (patient and/or physician) in physical possession of the images. The creation of these diagnostic images and duplicate copies is costly and cumbersome. Further, duplicate copies on physical media increases the security risk of unauthorized access.

Conventional secure online portal systems additionally suffer from problems with respect to the distribution of diagnostic images associated with a report. In these systems, electronic access to images requires a unique uniform resource locator (URL), username and password. However, URLs, usernames, and passwords are frequently lost or mistyped. The time lost locating these images is problematic in this environment because of the limited amount of time each patient can spend with a physician during a visit. Further, electronic access to the images is only controlled by the imaging facility (hospital) and not by the patient and/or physicians.

Accordingly, improved methods and systems for accessing images associated with diagnostic reports are desired.

BRIEF SUMMARY OF THE DISCLOSURE

According to various embodiments of the disclosed methods and systems, systems and methods for distributing and accessing digital diagnostic images associated with a hardcopy diagnostic imaging report are illustrated. A DICOM server receives and stores a diagnostic image and diagnostic information received from an imaging facility based on an imaging study. Thereafter, the DICOM server generates a diagnostic imaging report based on received diagnostic input parameters relating to the diagnostic and diagnostic information of the imaging study. The generated diagnostic imaging report includes a barcode comprising an embedded file path to one or more of the stored diagnostic images.

In one embodiment the embedded file path is a shortened URL and the barcode is a QR code. In implementations of this embodiment, the stored diagnostic images are DICOM persistent objects and generating the diagnostic imaging report includes constructing the shortened URL from an original URL by applying predefined rules based on Web Access to DICOM persistent objects. The URL may be constructed based on a unique identifier from the DICOM Tag Study Instance UID.

In one embodiment, a scanning device is configured to scan the barcode from a hardcopy diagnostic imaging report, access the file path embedded in the barcode, and display the one or more diagnostic images at the accessed file path. The scanning device may include a camera, a barcode reader for scanning the barcode with the camera and extracting the file path embedded in the scanned barcode, a network connectivity interface configured to access the diagnostic image at the extracted file path, and a display configured to display the content of the extracted file path.

Other features and aspects of the disclosed method and system will become apparent from the following detailed description, taken in conjunction with the accompanying drawings, which illustrate, by way of example, the features in accordance with embodiments of the disclosure. The summary is not intended to limit the scope of the claimed disclosure, which is defined solely by the claims attached hereto.

BRIEF DESCRIPTION OF THE DRAWINGS

The figures are provided for purposes of illustration only and merely depict typical or example embodiments. They do not limit the breadth, scope, or applicability of the invention.

DETAILED DESCRIPTION

Figure 1:
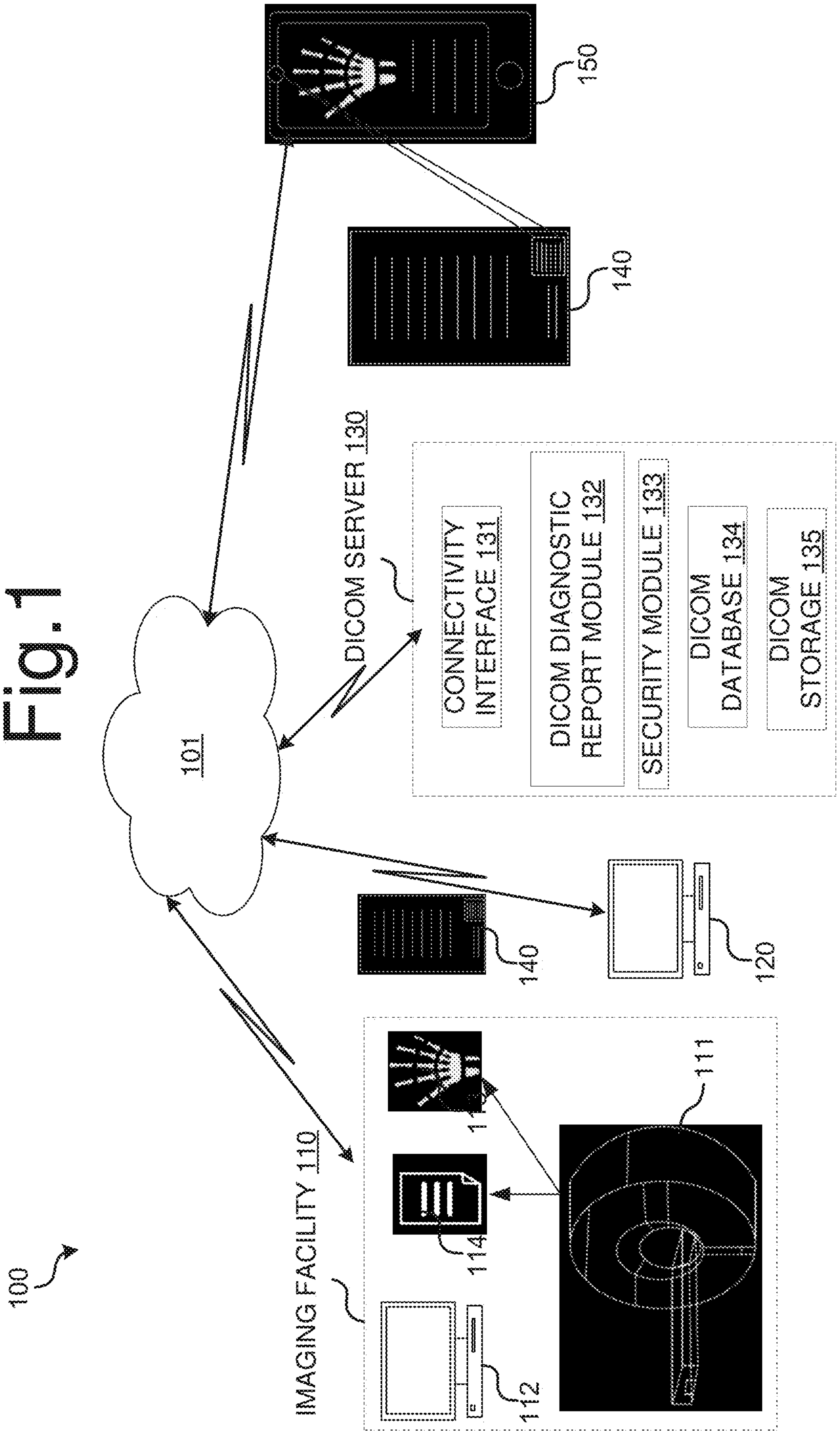
FIG. 1 illustrates an example diagnostic imaging report generation and distribution environment for implementing the systems and methods of the present disclosure.

FIG. 1 illustrates an example diagnostic imaging report generation and distribution environment 100 for implementing the systems and methods of the present disclosure. As illustrated in FIG. 1, a patient undergoes a diagnostic imaging study at imaging facility 110 using medical modality 111. Diagnostic images 113 and diagnostic information 114 related to the study are generated using medical modality 111 and workstation 112. Diagnostic images 113 and related diagnostic information 114 follow the Digital Imaging and Communications in Medicine (DICOM) standard for handling, storing, printing and transmitting medical imaging information. In this embodiment, diagnostic images 113 comprise tags for identification and grouping purposes.

The generated diagnostic images 113 and diagnostic information 114 are transmitted via communication medium 101 to a DICOM server 130. Communication medium 101 may comprise a communications network such as a cellular telephone network, a local area network (LAN), a wireless LAN (WLAN), a wide area network (WAN), a personal area network (PAN), a portion of the Internet, or any combination thereof. The medium 120 may be a wireless network system such as a cellular network, a satellite network, a wireless personal area network, a wireless local area network, a Bluetooth system, or other similar communication medium. The medium alternatively may be a wired system, such as a coaxial cable system, a fiber optic cable system, an Ethernet cable system, a USB system, or other similar communication medium.

DICOM Server 130 comprises a connectivity interface 131 for interfacing via communication medium 101, a DICOM diagnostic report module 132, a security module 133, DICOM database 134, and DICOM storage 135. Diagnostic report server 130 stores received diagnostic images 113 and diagnostic information 114 in DICOM storage 135. DICOM database 134 may perform administrative functions related to the administration and retrieval of stored diagnostic data, including the management of DICOM storage 135 and security module 133. Security module 133 is configured to authenticate any medical workstation 120 that attempts to access any stored diagnostic data such as diagnostic images 113, diagnostic information 114, or a generated diagnostic imaging report 140. Security module 133 may use any number of authentication methods for authenticating a medical workstation that accesses the stored diagnostic images and diagnostic information. For example, it may use password authentication, digital signature authentication, IP SEC authentication, Secure Sockets Layer (SSL) authentication, public-key cryptography authentication, etc.

In one embodiment, diagnostic report 140 is generated by diagnostic report module 132. In this embodiment, DICOM server 130 receives diagnostic report input parameters from a medical workstation (e.g. 120 or 112) over communication medium 101 and uses the diagnostic report input parameters to create and store diagnostic report 140. In implementations of this embodiment, components of the diagnostic report module may be distributed between the medical workstation 120 and server 130.

Figure 2A:
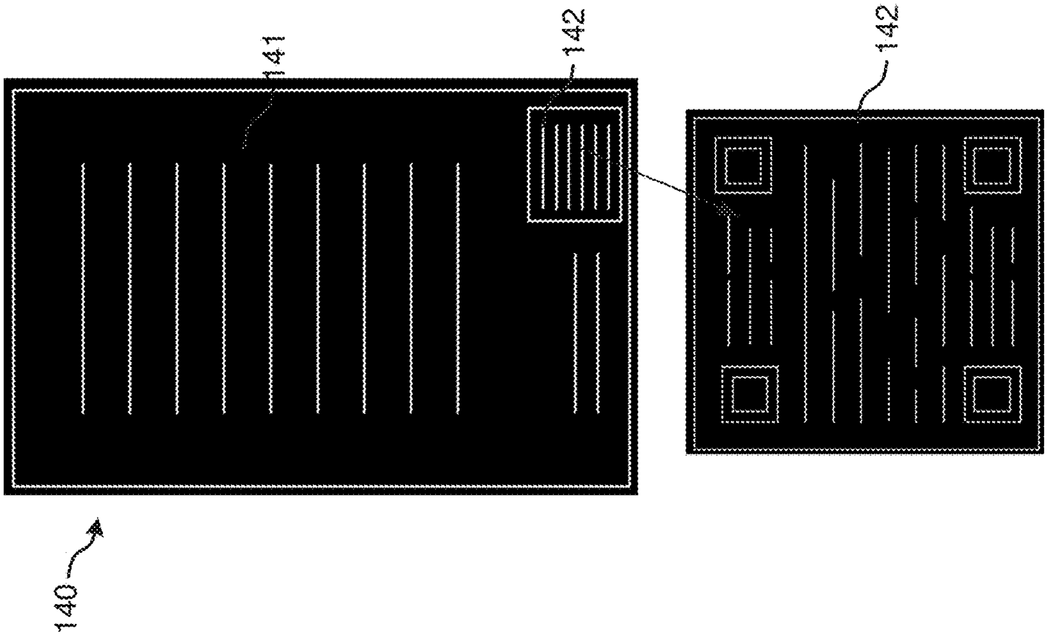
FIG. 2A is an exemplary diagnostic imaging report that may be used in implementations of the present disclosure.
Figure 2B:
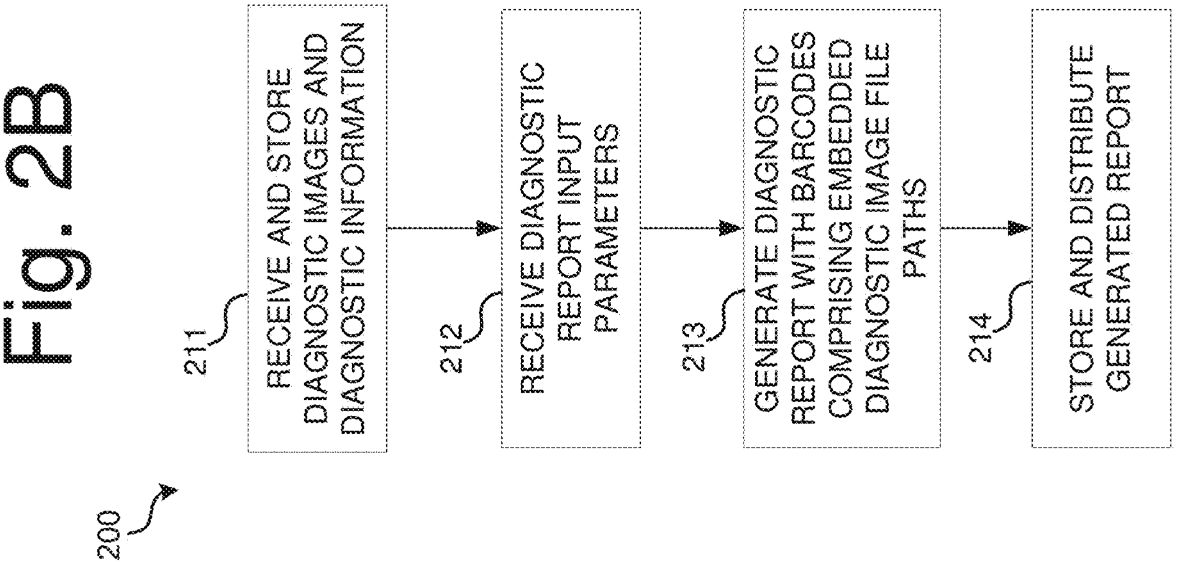
FIG. 2B is an operational flow diagram illustrating an exemplary method of generating the diagnostic imaging report of FIG. 2A.

FIG. 2A illustrates a page of an exemplary diagnostic imaging report 140 that may be used in implementations of the present disclosure. Diagnostic imaging report 140 will be discussed with reference to FIG. 2B, which is an operational flow diagram illustrating an exemplary method 200 of generating report 140.

At operation 211, diagnostic report server 130 receives and stores diagnostic images 113 and diagnostic information 114 that may be used by a medical workstation 120 for preparing a diagnostic imaging report 140. In one embodiment, the received diagnostic information and diagnostic images are stored at DICOM storage 135 of server 130. DICOM storage 135 may comprise one or more local or remote content file servers configured to store DICOM data. Access to the stored DICOM data is administered by DICOM database 134.

In one particular embodiment, each of diagnostic images 114 is stored at a file path of one or more content file servers of DICOM storage 135. In one embodiment, DICOM database 134 stores the file path for each of the diagnostic images. The file path may be designated as a Uniform Resource Location (URL). Each file path may comprise one or more diagnostic images and optionally text associated with the diagnostic image. For example, diagnostic images from the same study may all be stored at the same file path. Alternatively, each file path may store one diagnostic image or a subset of related diagnostic images from a study.

At operation 212, server 130 receives diagnostic imaging report input parameters from an interpreting physician operating a workstation 120 for generating a diagnostic imaging report. The diagnostic imaging report input parameters may comprise selected diagnostic images, selected diagnostic information, additional content added by the operator of medical workstation 120, an arrangement of the report content, etc. Diagnostic report module 132 receives these diagnostic imaging report input parameters and generates a diagnostic imaging report 140, which is stored on DICOM storage 135. All information in the report is uniquely generated for every imaging study performed.

At operation 213, diagnostic imaging report 140 is generated using DICOM diagnostic report module 132. The generated diagnostic imaging report 140 comprises textual diagnostic information 141 related to a diagnostic imaging study and one or more barcodes 142 comprising embedded file paths for diagnostic images associated with the textual diagnostic information 141. Additionally, the generated diagnostic imaging report 140 may further comprise generalized information such as the patient's demographics, institution details, and links for online access to the diagnostic information. In one particular embodiment, the hard copy version of diagnostic imaging report 140 is at least 70 millimeters in width and 105 millimeters in height.

Barcode 142 is any barcode capable of embedding a file path (e.g. a two-dimensional code such as a QR code, a color barcode, or a data matrix or a three-dimensional code.) In further embodiments, barcode 142 may embed additional information such as image identification information (e.g. patient name, identification of medical modality 111, identification of imaging facility 110, diagnostic image number, date of diagnostic image, etc.) and file path access information (e.g. login/password, encryption key, etc.) for accessing the diagnostic image at the associated file path. In one particular embodiment, the barcode 142 is a square with minimum dimension of 2.5 centimeters when printed as a hardcopy.

In one particular embodiment, the embedded file path is a URL for accessing diagnostic images associated with a hardcopy of a diagnostic imaging report. The URL may be a shortened form of the actual URL generated using a URL shortening service. Construction of the shortened URL may follow predefined rules. In one embodiment, the shortened URL is constructed as defined by Web Access to DICOM Persistent Objects (WADO). For example, the URL may be constructed using a unique identifier (UID) from the DICOM Tag Study Instance UID. As another example, the URL may be constructed as to avoid any reference to patient demographic information in the URL to avoid transmitting any unencrypted Protected Health Information (PHI) across the Internet. In the described embodiments, the URL may use the Hypertext Transfer Protocol Secure (HTTPS) protocol. In one embodiment, barcodes in electronic copies of generated report 140 include clickable file paths, thereby allowing immediate access to diagnostic images associated with the report.

Following the generation of report 140, at operation 214 report 140 is stored at DICOM storage 135 and distributed. Upon approval of the interpreting physician, the report is distributed to the patient and/or physicians that require a copy of the report. Copies of the report may be distributed through conventional distribution channels. For example, the report may be 1) printed and distributed as a hardcopy; 2) distributed via facsimile; 3) stored on any portable digital recording media; 4) emailed; and/or 5) made available electronically via an online portable. Because file paths to the diagnostic images of report 140 are embedded in one or more codes 142, distribution of the disclosed report does not require ancillary distribution of the diagnostic images.

Figure 3A:
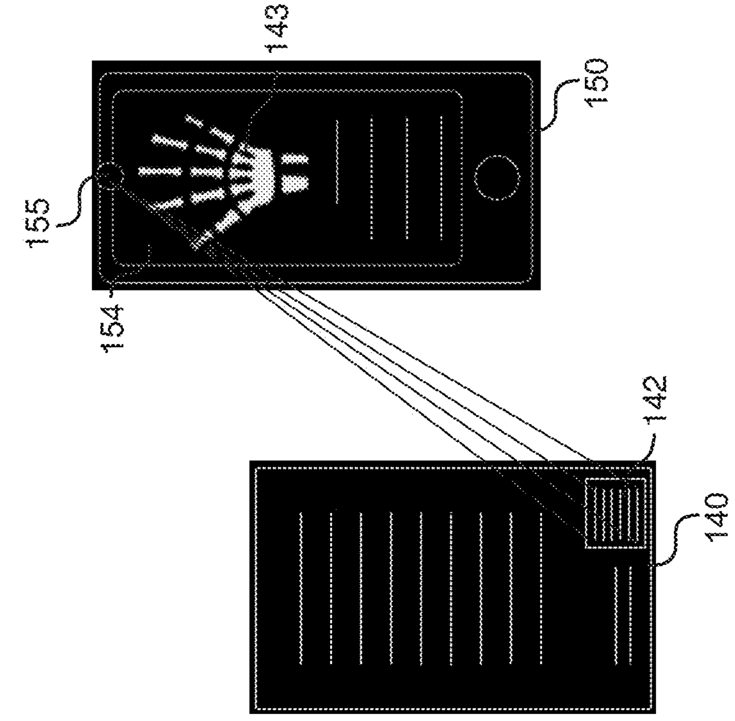
FIG. 3A is an exemplary scanning device that may be used to scan the barcode of the diagnostic imaging report of FIG. 2A.
Figure 3B:
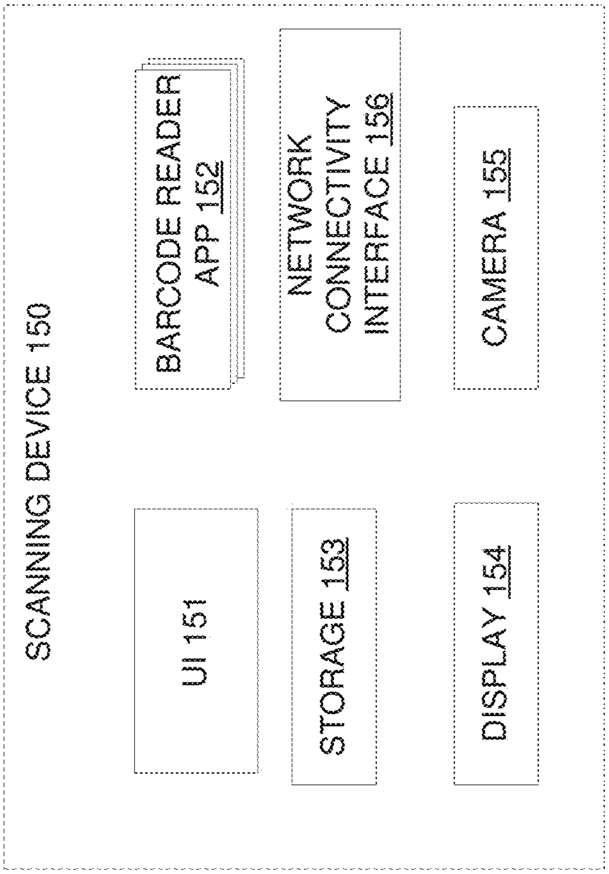
FIG. 3B is a high-level block diagram of a scanning device that may be used to scan the barcode of the diagnostic imaging report of FIG. 2A.

With reference now to accessing the diagnostic images associated with a hardcopy diagnostic imaging report, FIG. 3A is an exemplary scanning device 150 that may be used to scan the barcode 142 of diagnostic imaging report 140. FIG. 3B is a high-level block diagram of scanning device 150. A patient or physician operates scanning device 150 to scan barcode 142 and quickly and efficiently access diagnostic images associated with a hardcopy of diagnostic imaging report 140. Scanning device 150 may comprise any computing device (smartphone, cellphone, laptop, tablet, laptop-tablet hybrid, workstation with dedicated barcode reader, etc.) configured to scan barcode 142, access the file path embedded in barcode 142, and display the diagnostic image at the accessed file path.

Scanning device 150 may comprise a user interface (UI) 151, code reader application 152, storage 153, external or integrated display 154, camera 155, and network connectivity interface 156 for connecting to a network that can access diagnostic images associated with diagnostic imaging report 140. A user of scanning device 150 accesses barcode reader application 152 via UI 151 and reads barcode 142 using a camera 155 of sufficient resolution. A diagnostic image 143 associated with diagnostic imaging report 140 is subsequently displayed on display 154.

Figure 4:
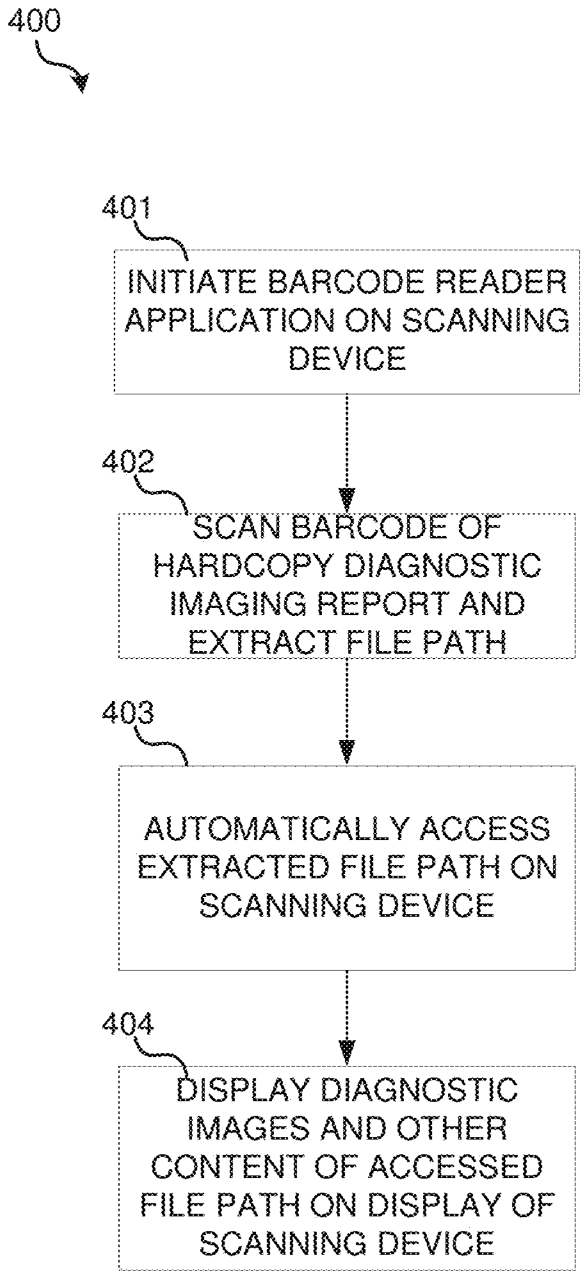
FIG. 4 is an operational flow diagram illustrating an exemplary process for retrieving diagnostic images associated with a diagnostic imaging report.

This process of retrieving diagnostic images will now be described in greater detail with reference to FIG. 4, which is an operational flow diagram illustrating an exemplary process 400 for retrieving diagnostic images associated with hardcopy diagnostic imaging report 140. At operation 401, a user of scanning device 150 initiates barcode reader application 152 via user interface 151 in preparation for scanning barcode 142 of diagnostic imaging report 140. Initiation of barcode reader application 152 prepares camera 155 of scanning device 150 to perform a read operation of barcode 142.

In some embodiments, barcode reader application 152 is a conventional barcode reading application configured to read and interpret a barcode of the same type as barcode 142. For example, if barcode 142 is a QR code with an embedded file path associated with a diagnostic image, barcode reader application 152 is configured to extract this file path embedded in the QR code for access to the diagnostic image. In an alternative embodiment, barcode reader application 152 may be a proprietary barcode reading application with built in security measures. In this embodiment, for example, scanning device 150 may be need to registered or authenticated before the application can be installed. Additionally, the proprietary application may provide additional functionality such as reading and displaying DICOM data, extracting security information from the scanned barcode, and automatically authenticating scanning device 150 when the embedded file path is accessed (if the file path requires additional authentication).

At operation 402, a user of scanning device 150 scans the barcode with barcode reader application 152 by positioning camera 155 over barcode 142. During scanning operation 402, barcode reader application 153 extracts a file path (e.g. URL) embedded in barcode 142. In some embodiments, additional information may be extracted from barcode 142 such as image identification information (e.g. patient name, identification of medical modality 111, identification of imaging facility 110, diagnostic image number, date of diagnostic image, etc.) and file path access information (e.g. login/password, encryption key, etc.) for accessing the diagnostic image at the associated file path.

At operation 403, scanning device 150 automatically accesses the extracted file path via network connectivity interface 156. In one embodiment, scanning device 150 accesses the extracted file path via the Internet. In an alternative embodiment, scanning device 150 may access the extracted file path if it is connected to a local network of DICOM server 130 or to a network with access rights to DICOM server 130.

At operation 404, the content 143 (e.g. diagnostic image (s) and description) of the accessed file path is displayed on display 154. In one particular embodiment, the file path is a URL and content 143 is displayed on display 154 by opening the URL on a web browser installed on device 150. The webpage may be configured to render on various desktop and mobile web browsers independent of the underlying operating system used. In this embodiment, the content 143 of the displayed webpage renders without any additional authentication steps, thereby providing the benefit of immediate access to the stored diagnostic images associated with the hardcopy diagnostic imaging report 140.

In alternative embodiments, rendering of the webpage requires that scanning device have a built in DICOM reader. In yet further embodiments, rendering of the webpage requires authentication of the accessing device. In these embodiments, authentication may be automated by embedding authentication information into the barcode 142. For example, when barcode reader application 152 interprets code 142, it may extract and automatically enter the authentication information into the accessed file path.

The disclosed methods and systems for distributing and accessing diagnostic images associated with a hardcopy diagnostic imaging report provide several advantages over conventional systems and methods. First, the hassle of viewing the images through an online portal is removed. In particular, the images may be accessed without manually authenticating access to the images and without wasting time searching for the images. Second, hardcopy reports are easily distributed without the need to carry ancillary printouts of the diagnostic images or ancillary portable media containing the diagnostic images. A patient or physician simply scans the code printed on the report with a supported device and immediately accesses the diagnostic image associated with the hardcopy report. Lastly, the disclosed diagnostic imaging report may be integrated into existing diagnostic report distribution systems with minimal cost.

Figure 5:
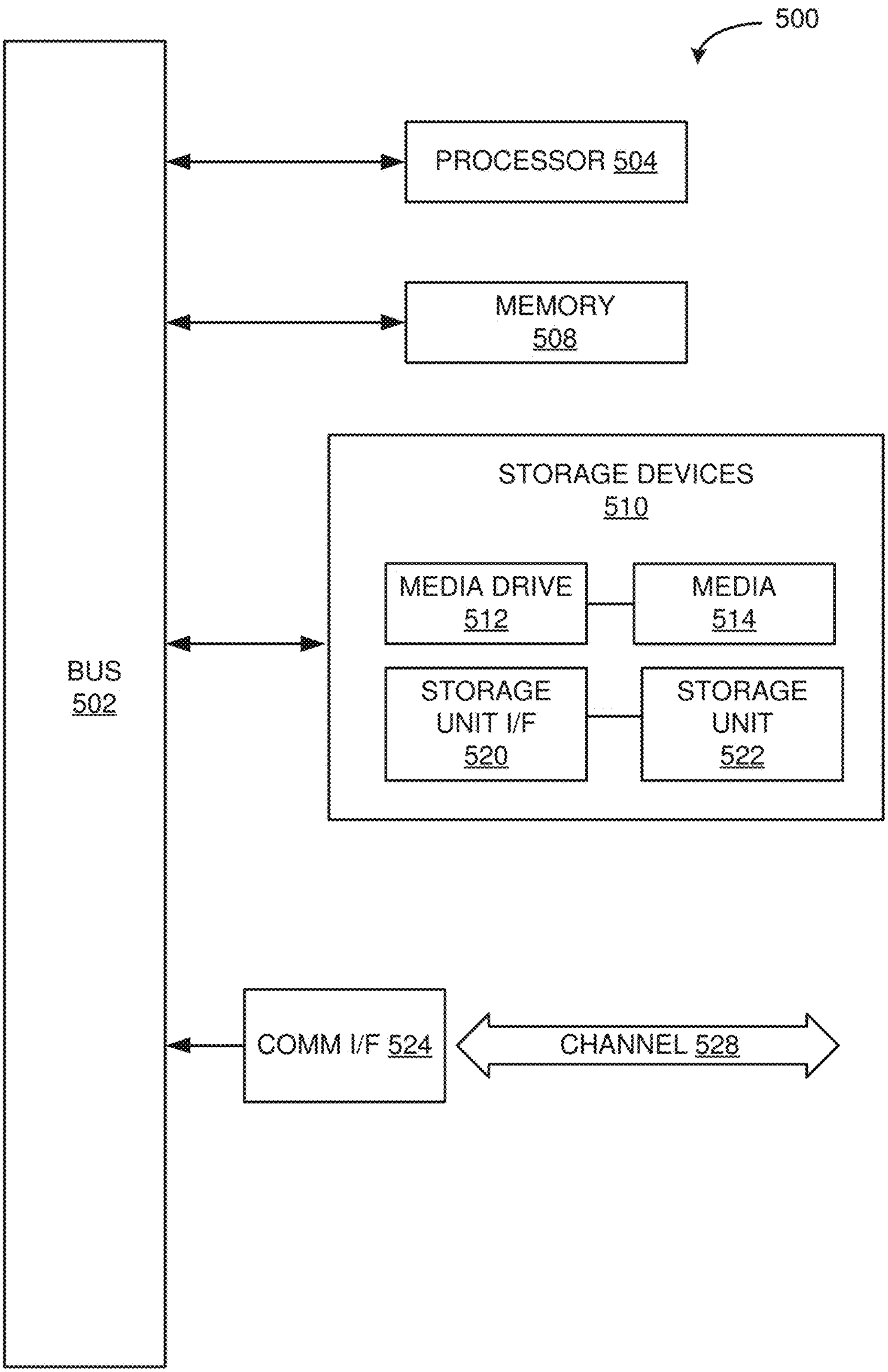
FIG. 5 is an example computing module that may be used to implement various features of the systems and methods disclosed herein.

FIG. 5 illustrates an example computing module that may be used to implement various features of the system and methods disclosed herein.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAS, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 5. Various embodiments are described in terms of this example-computing module 500. After reading this description, it will become apparent to a person skilled in the relevant art how to implement the application using other computing modules or architectures.

Referring now to FIG. 5, computing module 500 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random access memory (RAM) or other dynamic memory, might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a solid state drive, a magnetic tape drive, an optical disk drive, a CD or DVD drive (R or RW), or other removable or fixed media drive might be provided. Accordingly, storage media 514 might include, for example, a hard disk, an integrated circuit assembly, magnetic tape, cartridge, optical disk, a CD, DVD, Blu-ray Disc, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 1020. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A scanning device for accessing a diagnostic image associated with a hardcopy diagnostic imaging report, comprising:
- a camera;
- a barcode reader application configured to:
  - scan a barcode in the hardcopy diagnostic imaging report using the camera; and
  - extract a shortened uniform resource locator (URL) embedded in the scanned barcode, wherein:
  - the shortened URL is constructed from an original URL by applying predefined rules based on Web Access to DICOM Persistent Objects (WADO);
  - the original URL is a file path to the diagnostic image; and
  - the diagnostic image is a DICOM persistent object;
- a network connectivity interface configured to access the diagnostic image at the shortened URL; and
- a display; and
- a DICOM reader included in the barcode reader application and configured to display, via the display, the DICOM persistent object accessed at the shortened URL.

2. The scanning device of claim 1, wherein:
- the barcode is a QR code; and
- the shortened URL is automatically loaded on a web browser of the scanning device when the shortened URL is extracted.

3. The scanning device of claim 1, wherein the DICOM persistent object is retrieved from a DICOM server that receives and stores the diagnostic image and diagnostic information received from an imaging facility based on an imaging study associated with the hardcopy diagnostic imaging report.

4. The scanning device of claim 3, wherein the barcode reader application is further configured to extract from the barcode embedded URL access information for accessing the diagnostic image at the shortened URL.

5. The scanning device of claim 3, wherein;
- the DICOM server receives and stores the DICOM persistent object and diagnostic information from an imaging facility based on an imaging study;
- the DICOM server generates the hardcopy diagnostic imaging report based on diagnostic input parameters relating to the imaging study; and
- the DICOM server inserts the barcode comprising the shortened URL into the hardcopy diagnostic imaging report.

* * * * *